United States Patent [19]

Paulus et al.

[11] 4,166,122

[45] Aug. 28, 1979

[54] BIS-(5,5-DIMETHYL-1,3-OXAZOLIDIN-3-YL) METHANE AS AN ANTIMICROBIAL AGENT

[75] Inventors: Wilfried Paulus; Hermann Genth, both of Krefeld, Fed. Rep. of Germany

[73] Assignee: Bayer Aktiengesellschaft, Leverkusen, Fed. Rep. of Germany

[21] Appl. No.: 879,548

[22] Filed: Feb. 21, 1978

[30] Foreign Application Priority Data

Mar. 15, 1977 [DE] Fed. Rep. of Germany ....... 2711106

[51] Int. Cl.$^2$ .............................................. A61K 31/42
[52] U.S. Cl. ............................... 424/272; 260/307 FA
[58] Field of Search ................... 424/272; 260/307 FA

[56] References Cited

U.S. PATENT DOCUMENTS 2,194,314  3/1940  Maxwell ............................. 260/584

OTHER PUBLICATIONS

Danielson–C.A. 58, 12750b, (1963)–Abstract of Belg. Pat. 621923.

Primary Examiner—Raymond V. Rush
Attorney, Agent, or Firm—Sprung, Felfe, Horn, Lynch & Kramer

[57] ABSTRACT

5,5'-dimethyl-di-(1,3-oxazolidin-3-yl) methane, a process for its preparation of reacting a source of formaldehyde with isopropanolamine at elevated temperature followed by water removal, an anti-microbial composition comprising said 5,5'-dimethyl-di-(1,3-oxazolidin-3-yl) methane and a diluent and a process for combatting micro-organisms by applying 5,5'-dimethyl-di-(1,3-oxazolidin-3-yl) methane to a micro-organism containing sample.

3 Claims, No Drawings

BIS-(5,5-DIMETHYL-1,3-OXAZOLIDIN-3-YL) METHANE AS AN ANTIMICROBIAL AGENT

The present invention relates to 5,5'-dimethyl-di-(1,3-oxazolidin-3-yl) methane, its preparation and use.

In addition, a process for the preparation of 5,5'-dimethyl-di-(1,3-oxazolidin-3-yl)methane has been found in which isopropanolamine is reacted with an excess of formaldehyde at elevated temperature and water is then eliminated.

The preparation of the 5,5'-dimethyl-di-(1,3-oxazolidin-3-yl)methane according to the invention can be illustrated by the following equation:

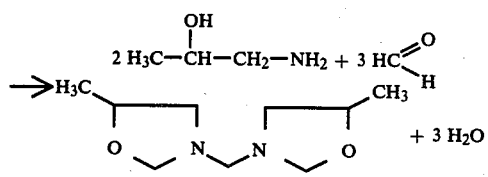

One can also use polymers of formaldehyde, for example paraformaldehyde, instead of formaldehyde.

The process according to the invention is carried out with an excess of formaldehyde. In order to achieve quantitative conversion of the isopropanolamine, at least 1.5 mols of formaldehyde are appropriately employed per mol of isopropanolamine. One can also carry out the process according to the invention with a larger amount of formaldehyde. For economic reasons, in general 1.5 to 3 mols, preferably 1.5 to 1.7 mols, of formaldehyde are employed per mol of isopropanolamine.

In general, the process according to the invention is carried out in the temperature range from 60° to 120° C., preferably from 70° to 90° C.

The process according to the invention can be carried out either without or with solvents. Solvents which can be used are liquids which do not change under the reaction conditions. Examples which may be mentioned are benzene and toluene.

The elimination of water can be effected, for example, by fractional distillation or by azeotropic distillation.

Azeotropic distillation can preferably be carried out with the aid of a water separator and an entraining agent, such as benzene and toluene.

The process according to the invention can be carried out, for example, as follows:

Formaldehyde is introduced in portions into the isopropanolamine and the reaction is carried out at the chosen reaction temperature. After the reaction, fractional or azeotropic distillation is carried out in order to eliminate the water. Pure 5,5'-dimethyl-di-(1,3-oxazolidin-3-yl)methane, which in general can be used without further purification, is obtained by distillation.

The 5,5'-dimethyl-di-(1,3-oxazolidin-3-yl) methane according to the invention can be a constituent of functional liquids which can be used for combating micro-organisms. In particular, the functional liquids according to the invention can be used for protecting industrial materials against microbial decomposition. Thus 5,5'-dimethyl-di-(1,3 orazolidin-3-yl)methane is an antimicrobial agent used to protect industrial materials.

It is also possible to employ, as a functional liquid, the 5,5'-dimethyl-di-(1,3-oxazolidin-3-yl)methane as the active compound alone or in customary formulations or in combinations with other active compounds.

Customary formulations are, for example, dilutions with water or alcohols or aqueous alcohols or organic solvents.

Examples which may be mentioned of possible active compounds which can be used in combinations with the active compound according to the invention are: reaction products of alcohols or amines with formaldehyde, chloracetamide or N-methylolchloroacetamide, pyridine thiol-1-oxide, 1,2-benzisothiazolone, 2-mercaptobenzthiazole and 2-bromo-2-nitropropane-1,3-diol.

Industrial materials are, for example lubricoolants, adhesives, coating compositions, rosin sizes, textile auxiliaries, dispersions, top coats and other aqueous paints, plasters and other aqueous solutions or suspensions which are susceptible to microbial decomposition. The functional liquids according to the invention are particularly suitable for preserving lubricoolants, coating compositions, adhesives, emulsions and polishes.

The functional liquids according to the invention have a powerful destructive or inhibiting action on micro-organisms. Examples of micro-organisms which may be mentioned are baceteria, fungi, yeasts, myxo-organisms, viruses and algae.

Examples of bacteria which may be mentioned are: *Escherichia coli, Pseudomonas fluorescens, Bacillus subtilis, Bacterium vulgare, Pseudomonas aeruginosa, Bacillus mycoides* and *Staphylococcus aureus*.

Examples of fungi and yeasts which may be mentioned are: *Penicillium glaucum, Rhizopus nigricans, Aspergillus niger, Torula utilis, Candida crusei* and *Candida albicans*.

Examples of algae and myxo-organisms which may be mentioned are: *Phaeodactylum tricornutum* Bohlin, *Euglena gracilis* Klebs, *Oscillatoria geminata* Meneghini, *Stichococcus bacillaris* Naegili and *Aerobacter aerogenes*.

The amount of the functional liquids employed depends on the species and occurrence of the micro-organisms, on the number of germs and on the medium. The optimum amount employed can, when used, in each case be easily determined, by test series. In general, however, it is sufficient to use 0.01% to 0.2% of the active compound, relative to the material to be protected from micro organisms.

The functional liquids according to the invention are colourless and readily soluble in water and organic solvents. They can advantageously be used in low concentrations.

EXAMPLE 1

960 g of paraformaldehyde (32 mols) are introduced in portions into 1,500 g (20 mols) of isopropanolamine. The reaction temperature is kept at about 70° C. by cooling the reaction vessel. After the reaction has subsided, the reaction mixture is kept at 80° C. for one hour. In order to eliminate the water, fractional distillation is then carried out. 1.710 g of 5,5'-dimethyl-di-(1,3-oxazolidin-3-yl)methane are obtained at boiling point$_{20}$ 123° C. (which corresponds to a yield of 92% of the quantitative conversion).

EXAMPLE 2

A lubricoolant based on mineral oil is diluted with water in the ratio of 1:20 and contaminated daily for 3 months with microbes from a microbially decayed oil emulsion. A number of germs which remains constant is already set up after a few days (about $10^7$ to $10^9$ germs/ml). In contrast, if the dilution used contains 0.1% of 5,5'-dimethyl-di-(1,3-oxazolidin-3-yl)methane, the lubricoolant is still germfree at the end of the test period.

EXAMPLE 3

5,5'-dimethyl-di-(1,3-oxazolidin-3-yl)methane was dissolved in a nutrient agar, which was prepared with beer wort and peptone, in each case in a graded concentration between 0.01 and 0.5% by weight per sample. After the agar had solidified, the agar samples thus prepared were contaminated with pure cultures of *Chaetomium globosum* Kunze, *Rhizopus nigricans* and *Asperigillus niger*.

The samples were evaluated after storing for two weeks at 28° C. and 60 to 70% relative atmospheric humidity. Table 1 which follows gives, as the minimum inhibitory concentration, the lowest concentration of the compound contained in an agar sample at which no growth at all of the species of microbe used took place.

Table 1

| Test organisms | Minimum inhibitory concentrations (% by weight) |
| --- | --- |
| *Chaetomium globosum* Kunze | 0.05 |
| *Rhizopus nigricans* | 0.1 |
| *Aspergillus niger* | 0.08 |

EXAMPLE 4

1% of caprolactum is added, as an additional source of carbon and nitrogen, to an Allen nutrient solution (Arch. Mikrobiol. 17, 34 to 53, (1952)), and, after sterilisation, the solution is infected with myxo-organisms which are isolated from spinning water circulations used in the manufacture of polyamide. In order to detect the antimicrobial action, 5,5'-dimethyl-di-(1,3-oxazolidin-3-yl)methane is added in increasing concentration to samples of the nutrient solution. The concentration at which the growth of the test organisms is prevented, after incubation at room temperature for three weeks, is determined, as the minimum inhibitory concentration. The minimum inhibitory concentration is 0.005%.

EXAMPLE 5

5,5'-dimethyl-di-(1,3-oxazolidin-3-yl)methane is dissolved, in increasing concentration, in agar broth samples. The agar broth samples are then contaminated with *Escherichia coli*, *Staphylococcus aureus* and *Pseudomonas aeruginosa*, stored at 28° C. and 60 to 70% relative atmospheric humidity and evaluated after two weeks. The results obtained are summarised in Table 2 which follows:

Table 2

| Test organisms | Minimum inhibitory concentrations (% by weight) |
| --- | --- |
| *Escherichia coli* | 0.01 |
| *Pseudomonas aeruginosa* | 0.02 |
| *Staphylococcus aureus* | 0.007 |

EXAMPLE 6

0,1% of 5,5'-dimethyl-di-(1,3-oxazolidin-3-yl)methane is added, as a preservative, to a coating composition based on starch and the composition is then contaminated with baceteria (*Escherichia coli* and *Pseudomonas aeruginosa*) and moulds (*Chaetomium globosum* and *Aspergillus niger*). After storing for forty-eight hours at room temperature, a determination of the number of germs shows that the coating composition is germfree, although the number of germs introduced was in the order of magnitude of $10^5$/g of coating composition. The viscosity and odour of the coating composition do not change. A balanced preserving effect is thus achieved. In constrast, the number of germs in a microbicide-free coating composition increases under the conditions indicated above to a constant value of $10^7$ germs/g. The viscosity is simultaneously reduced; the coating composition cannot be used.

What is claimed is:

1. A process for combatting a micro-organism which comprises applying to said micro-organism 5,5'-dimethyl-di-(1,3-oxazolidin-3-yl) methane.

2. A process according to claim 1 wherein said 5,5'-dimethyl-di-(1,3-oxazolidin-3-yl) methane is applied to said micro-organism in an amount of 0.01 to 0.2 weight percent based upon the amount of material containing the micro-organism.

3. A process for protecting an industrial material against microbicidal action which comprises applying to the industrial material 5,5'-dimethyl-di-(1,3-oxazolidin-3-yl)methane.

* * * * *

UNITED STATES PATENT AND TRADEMARK OFFICE
CERTIFICATE OF CORRECTION

PATENT NO. : 4,166,122
DATED : August 28, 1979
INVENTOR(S) : PAULUS et al.

It is certified that error appears in the above-identified patent and that said Letters Patent are hereby corrected as shown below:

Title Page, Title [54], "5,5" should read -- 5,5' --.

Column 1, line 1, "5,5" should read -- 5,5' --.

Column 2, line 24, "baceteria" should read -- bacteria --.

Column 3, line 37, "caprolactum" should read -- caprolactam --

Signed and Sealed this

Twenty-fifth Day of December 1979

[SEAL]

Attest:

SIDNEY A. DIAMOND

Attesting Officer

Commissioner of Patents and Trademarks